United States Patent [19]

Bossard et al.

[11] Patent Number: 5,119,030

[45] Date of Patent: Jun. 2, 1992

[54] APPARATUS FOR ELECTRICALLY INSPECTING THE SURFACE OF A DRUM

[75] Inventors: Peter R. Bossard, Langhorne, Pa.; Kevin D. Brown, Gasport; Charles Hagen, Lockport, both of N.Y.

[73] Assignee: Trek, Inc, Medina, N.Y.

[21] Appl. No.: 526,063

[22] Filed: May 18, 1990

[51] Int. Cl.$^5$ ............................................. G01N 27/61
[52] U.S. Cl. ..................................... 324/456; 324/455
[58] Field of Search .................. 324/452, 454–458; 355/202, 216

[56] References Cited

U.S. PATENT DOCUMENTS 4,367,948  1/1983  Suzuki ................................ 355/216
4,780,680  10/1988  Reuter et al. ....................... 324/455

Primary Examiner—Jack B. Harvey
Attorney, Agent, or Firm—Hodgson, Russ, Andrews, Woods & Goodyear

[57] ABSTRACT

Apparatus for determining the physical uniformity of a charged drum surface wherein current signals are induced in sensing electrodes in response to variation in drum surface charge. The sensing electrodes are on a detector assembly which is movable toward the drum for inspection of the surface and movable away from the drum after inspection when the drum is to be ejected from the apparatus. The detector assembly is movable through another degree of freedom to accommodate irregularities in drum geometry encountered during rotation thereof. The detector assembly also is provided with structure for maintaining a predetermined spacing of the sensing electrodes from the drum surface during relative movement therebetween. The drum is received, held, and rotated by co-operation between a drum retention assembly and a drum clamping mechanism. The retention assembly includes an arrangement of retainer arms which contact the drum inner surface and which are collapsed in response to forcible engagement of the drum by the drum clamping mechanism to allow rotation of the drum. The drum clamping mechanism is adjustable in two directions to accommodate various drum geometries, and it is movable away from the drum after inspection when the drum is to be ejected. An eject mechanism operatively associated with the drum retention assembly moves an inspected drum out of the apparatus to allow entry of a next drum to be inspected.

9 Claims, 9 Drawing Sheets

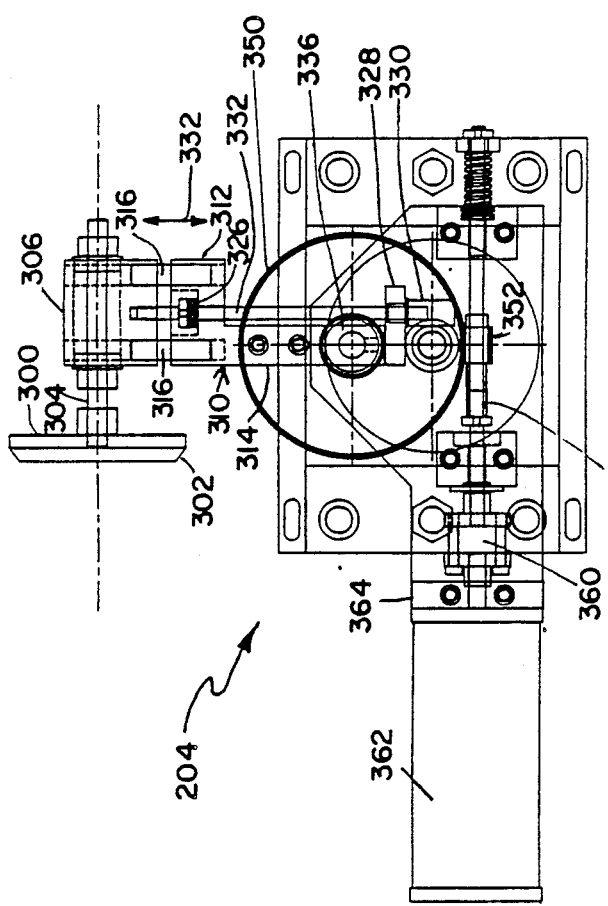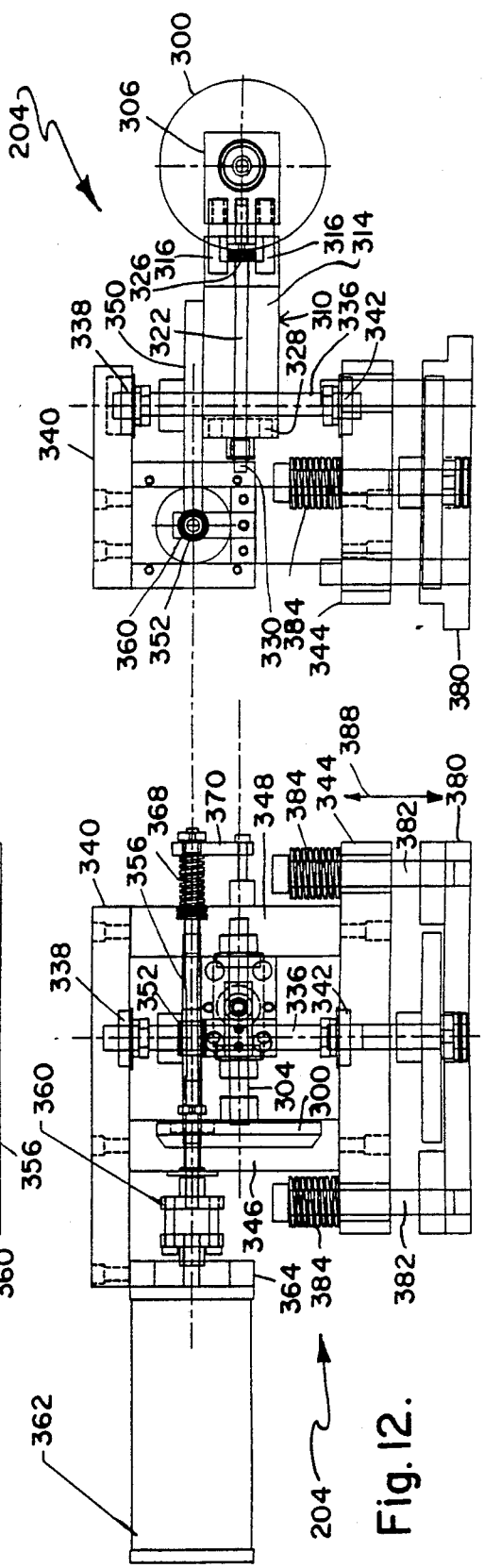

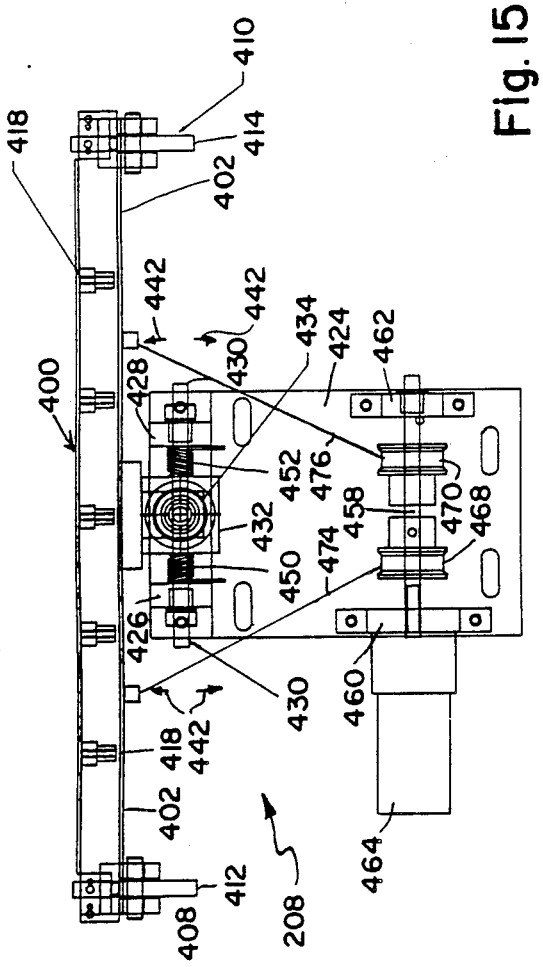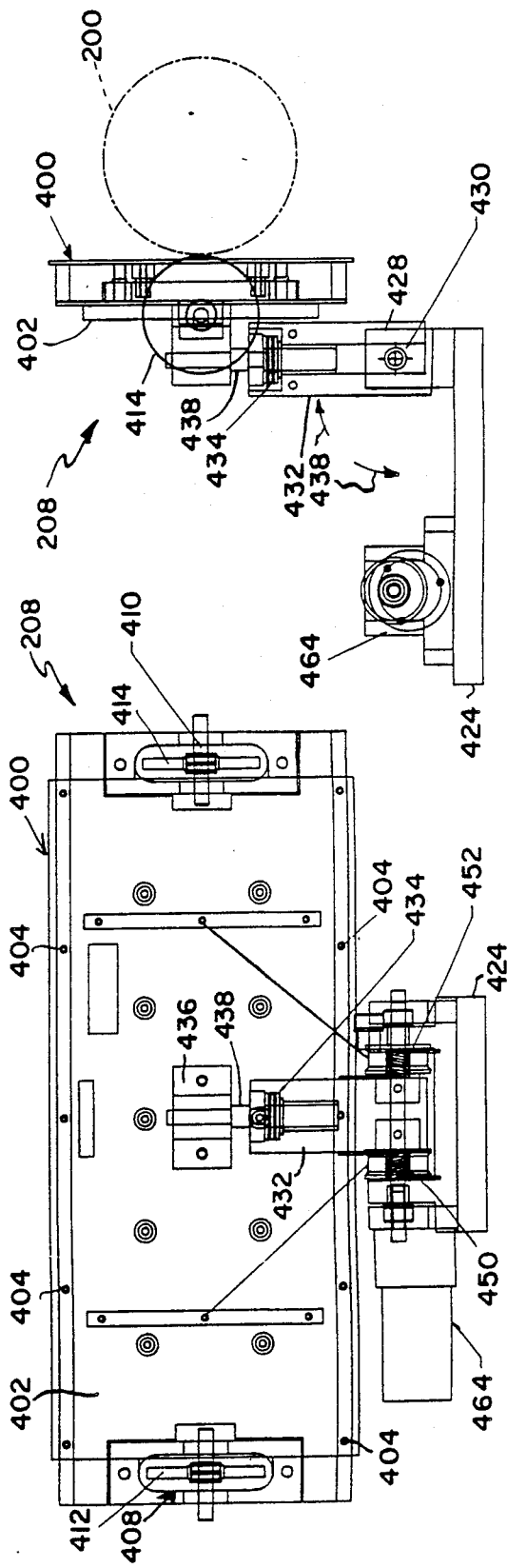

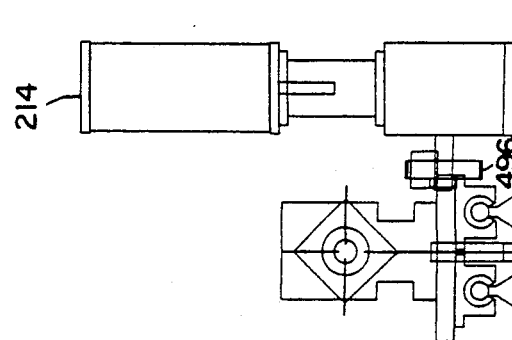
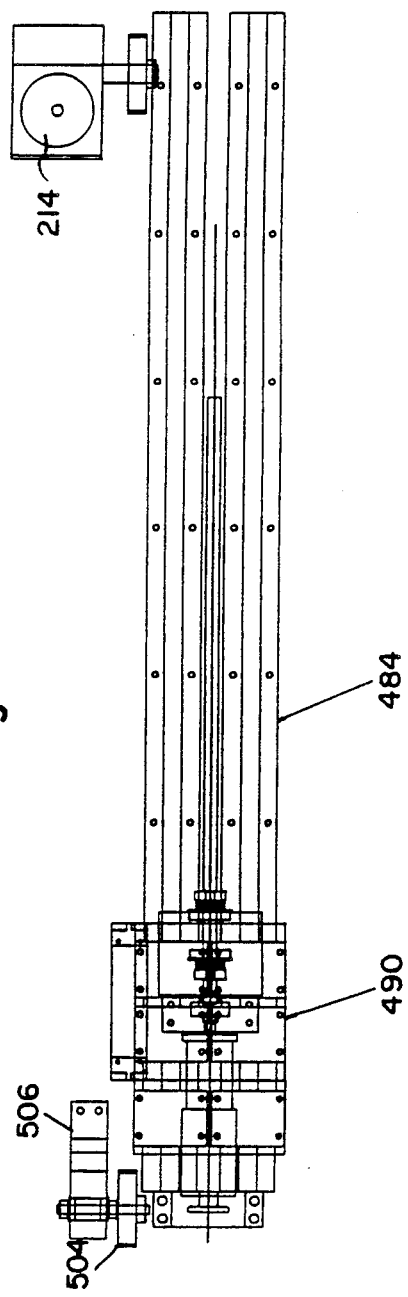
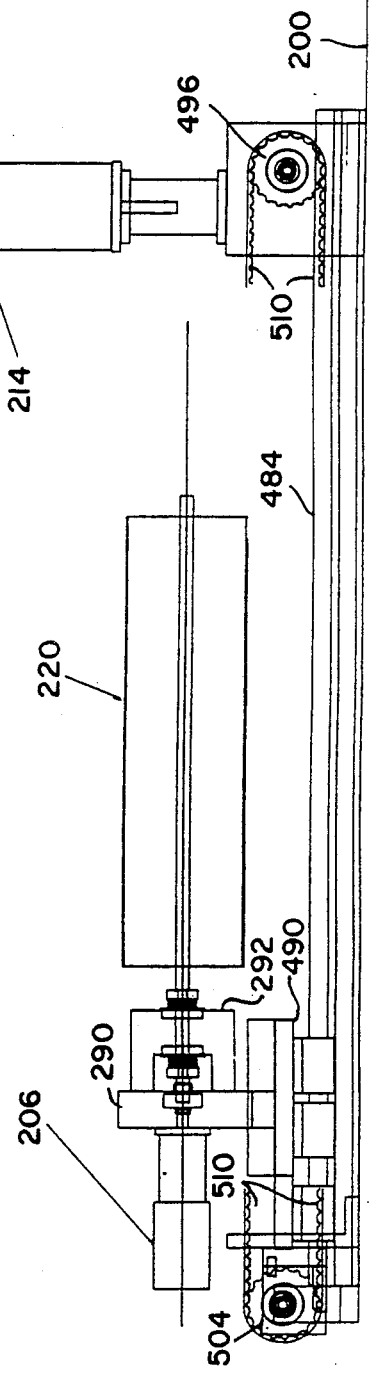

APPARATUS FOR ELECTRICALLY INSPECTING THE SURFACE OF A DRUM

BACKGROUND OF THE INVENTION

This invention relates to the electrostatic measurement art, and more particularly to a new and improved inspection apparatus for determining the physical uniformity of a surface capable of being electrically charged.

One area of use of the present invention is in determining the surface quality and uniformity of photoconductive drums used in photocopiers, although the principles of the present invention can be variously applied to inspecting any drum surface capable of holding electrical charge. Heretofore, photoconductive drums have been inspected visually or by light scattering techniques to determine the presence of surface defects such as holes. These approaches, however, are indirect in that they provide no measure of charge properties of the drum surface and they provide information only about the reflective properties of the surface.

It would, therefore, be highly desirable to provide an apparatus for quickly and reliably determining the physical quality and uniformity of a charged drum surface in a manner providing a measure of the charge properties of the surface. It would also be highly desirable to provide in such apparatus the capabilities of accommodating variations in drum surfaces, effectively holding the drums during inspection, and rapid automatic removal of a drum from the apparatus upon completion of inspection.

SUMMARY OF THE INVENTION

It is, therefore, a primary object of this invention to provide a new and improved apparatus for determining the physical uniformity of a drum surface capable of being electrically charged.

It is a further object of this invention to provide such apparatus which rapidly and directly measures the charge density on the drum surface.

It is a further object of this invention to provide such apparatus wherein detected electrical signals are of high resolution.

It is a further object of this invention to provide such apparatus wherein electrical noise is minimized.

It is a further object of this invention to provide such a method and apparatus having the capability of determining the size, number and location of surface defects.

The present invention provides apparatus for determining the physical uniformity of a drum surface capable of holding electrical charge wherein plurality of sensing electrodes each having an edge are located in close physical proximity to the drum surface and is disposed so that upon relative movement between the drum surface and sensing electrodes, charge on the drum surface crosses the edges of the electrodes. Electrical charge is applied to the drum surface and relative movement is provided between the drum surface and sensing electrodes while maintaining a constant distance therebetween. Current signals are induced in the sensing electrodes in response to a variation in the surface charge crossing the edges of the electrodes, and the signals are detected and electrical parameters thereof are measured to provide information on the charge density of the surface to determine the physical uniformity of the surface.

The sensing electrodes are on a detector assembly which is movable toward the drum for inspection of the surface and movable away from the drum after inspection when the drum is to be ejected from the apparatus. The detector assembly is movable through another degree of freedom to accommodate irregularities in drum geometry encountered during rotation thereof. The detector assembly also is provided with means for maintaining a predetermined spacing of the sensing electrodes from the drum surface during relative movement therebetween. The drum is received, held, and rotated by co-operation between a drum retention assembly and a drum clamping mechanism. The retention assembly includes an arrangement of retainer arms which contact the drum inner surface and which are collapsed in response to forcible engagement of the drum by the drum clamping mechanism to allow rotation of the drum. The drum clamping mechanism is adjustable in two directions to accommodate various drum geometries, and it is movable away from the drum after inspection when the drum is to be ejected. An eject mechanism operatively associated with the drum retention assembly moves an inspected drum out of the apparatus to allow entry of a next drum to be inspected.

The foregoing and additional advantages and characterizing features of the present invention will become clearly apparent a reading of the ensuing detailed description together with the included drawings wherein:

BRIEF DESCRIPTION OF THE DRAWING FIGURES

FIG. 12 is a front elevational view of the drum capture mechanism of the apparatus of FIGS. 6–8;

FIG. 13 is a top plan view thereof;

FIG. 14 is an end elevational view thereof;

FIG. 15 is a rear elevational view of the detector assembly of the apparatus of FIGS. 6–8;

FIG. 16 is a top plan view thereof;

FIG. 17 is an end elevational view thereof;

FIG. 18 is a fragmentary front elevational view of the drum eject mechanism of the apparatus of FIGS. 6–8;

FIG. 19 is a top plan view thereof; and

FIG. 20 is an end elevational view thereof.

DETAILED DESCRIPTION OF THE ILLUSTRATED EMBODIMENT

Figure 1:
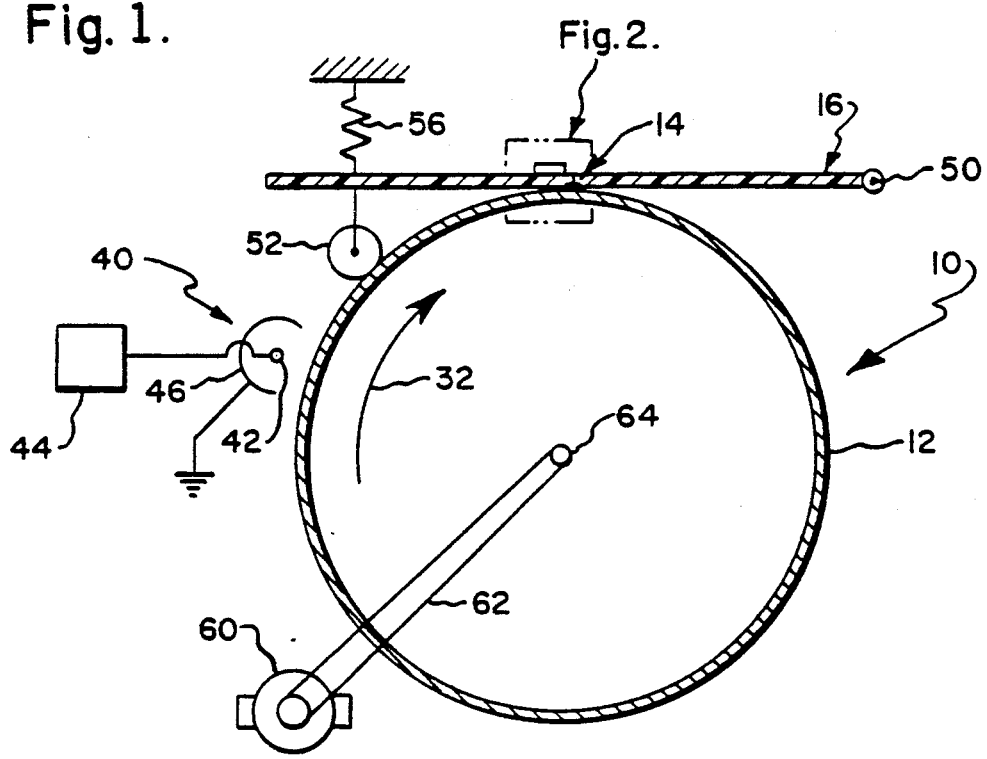
FIG. 1 is a schematic diagram illustrating the method and apparatus of the present invention.

FIG. 1 illustrates the basic principles of the apparatus according to the present invention for determining the physical uniformity, integrity, or homogeneity of a drum surface capable of holding electrical charge. A photoconductive drum 10 of the type employed in photocopiers is shown in cross-section and has an outer surface 12 which is to be inspected for defects such as holes. The apparatus according to the present invention comprises at least one sensing electrode generally designated 14 and means generally designated 16 for locating electrode 14 in close proximity to surface 12. As shown more clearly in FIG. 2, electrode 14 according to the present invention has an edge 18 and is disposed so that upon relative movement between surface 12 electrode 14, electrical charge on surface 12 crosses edge 18 of electrode 14 in a manner which will be described in further detail presently.

The electrode supporting and locating means 16 is in the form of a printed circuit board rectangular in overall shape having a length commensurate with the axial length of drum 10 or corresponding dimension of any other surface being inspected, and having a width sufficient to accommodate circuit components on the side opposite electrode 14 as will be explained in further detail presently. Electrode 14 can be formed on the surface of board 16 by deposition, etching, or other suitable techniques well-known to those skilled in the art. In accordance with the present invention, electrode 14 has a surface area facing surface 12 which is sufficiently small so as to minimize electrical noise when electrode 14 is in close proximity to surface 12. In particular, electrode 14 is rectangular in shape wherein edge 18 extends lengthwise thereof and a second edge 20 extends parallel to edge 18 along the opposite side of electrode 14. Edges 18, 20 are joined by a pair of opposite edges, one of which is designated 22 in FIG. 2. By way of example, in an illustrative apparatus, electrode 14 is of tin-plated or gold-plated copper having a length of about 6 mm and a width of about 0.381 mm. Electrode 14 is connected by an electrical lead or conductor 28 to circuit components on the opposite side of load 16, one such component being designated 10 in FIG. 2.

Figure 2:
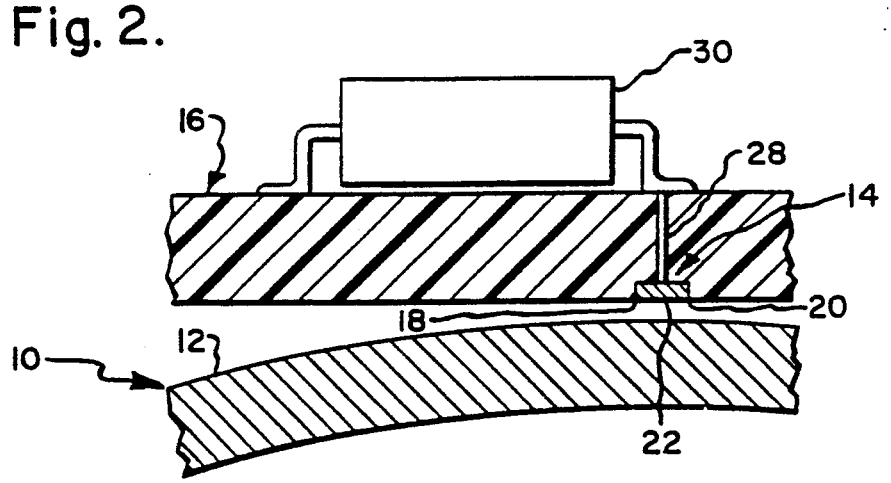
FIG. 2 is an enlarged schematic diagram of a portion of the apparatus of FIG. 1.

For inspecting most surfaces, the apparatus of the present invention includes a plurality of sensing electrodes each like electrode 14 arranged in a path extending in a direction generally cross-wise of the direction of relative movement between the electrodes and the surface. For example, in the arrangement illustrated in FIG. 1, the direction of rotation of drum 10 indicated by arrow 2 is in the plane of the paper, and therefore the plurality of sensing electrodes like electrode 14 extend along a path generally normal to the plane of the paper. FIG. 2 illustrates a typical arrangement of sensing electrodes on board 16 wherein, for example, 12 sensing electrodes are arranged along a path generally parallel to the lonqitudinal axis of board 16. This path extends cross-wise of the direction of relative movement between sensing electrodes and surface, i.e., in a direction parallel to the axis of rotation of drum 10 in the arrangement in FIG. 1. Three successively adjacent sensing electrodes are designated 14, 14', and 14", respectively. Alternate electrodes, i.e. 14 and 14" are in end-to-end alignment and the intermediate one, i.e. electrode 14' is slightly offset laterally and in slightly lonqitudinal overlapping relation with the corresponding ends of electrodes 14 and 14". This arrangement ensures that the entire portion of the surface will pass along the arrangement of electrodes and be sensed thereby. Each of the electrodes is connected to a corresponding lead or conductor, i.e. 28, 28', 28", to circuit components or the opposite side of board 16 which will be described in detail presently. While 12 sensing electrodes have been shown in the illustrative arrangement of FIG. 3, the total number is variable, depending upon the sizes of the various surfaces being measured, for example on the range of axial lengths of photoconductive drums being inspected.

The apparatus of the present invention further comprises means 40 for applying electrical charge to the surface being inspected. In the illustrative arrangement of FIG. 1 for inspecting surface 12 of the photoconductive drum 10, charging means 40 typically comprises a charging electrode in the form of a wire 42 extending longitudinally along and in closely spaced parallel relation to drum surface 12, a source of high DC voltage 44 connected electrically to wire 42 and a shield 46 located outwardly of wire 42 and surface 12 are typically connected electrically to ground.

In accordance with the present invention, a constant distance is maintained between sensing electrode 14 and surface 12 during relative movement therebetween. This can be accomplished by various suitable means, and in the arrangement of FIG. 1, board 16 is pivotally movable about point 50, a roller 52 rotatably mounted on board 16 contacts drum 10 and establishes a predetermined constant direction or spacing between the surface of the board 16 containing electrodes 14, and a biasing means 56 acts on board 16 urging roller 52 against drum 10. Various other mechanical arrangements can of course be employed.

There is also provided means for causing relative movement between surface 12 and sensing electrodes 14. In the arrangement shown, surface 12 is moved and to this end drum 10 is rotated by means including a drive motor 60 drivingly coupled through a pulley 62 to a shaft 64 upon which drum 10 is mounted for rotation. Various other mechanical drive arrangements can of course be employed. While in the present illustration surface 12 is moved relative to sensors 14, there may be other applications of the present invention wherein it may be feasible to move the sensors relative to the surface.

Figure 4:
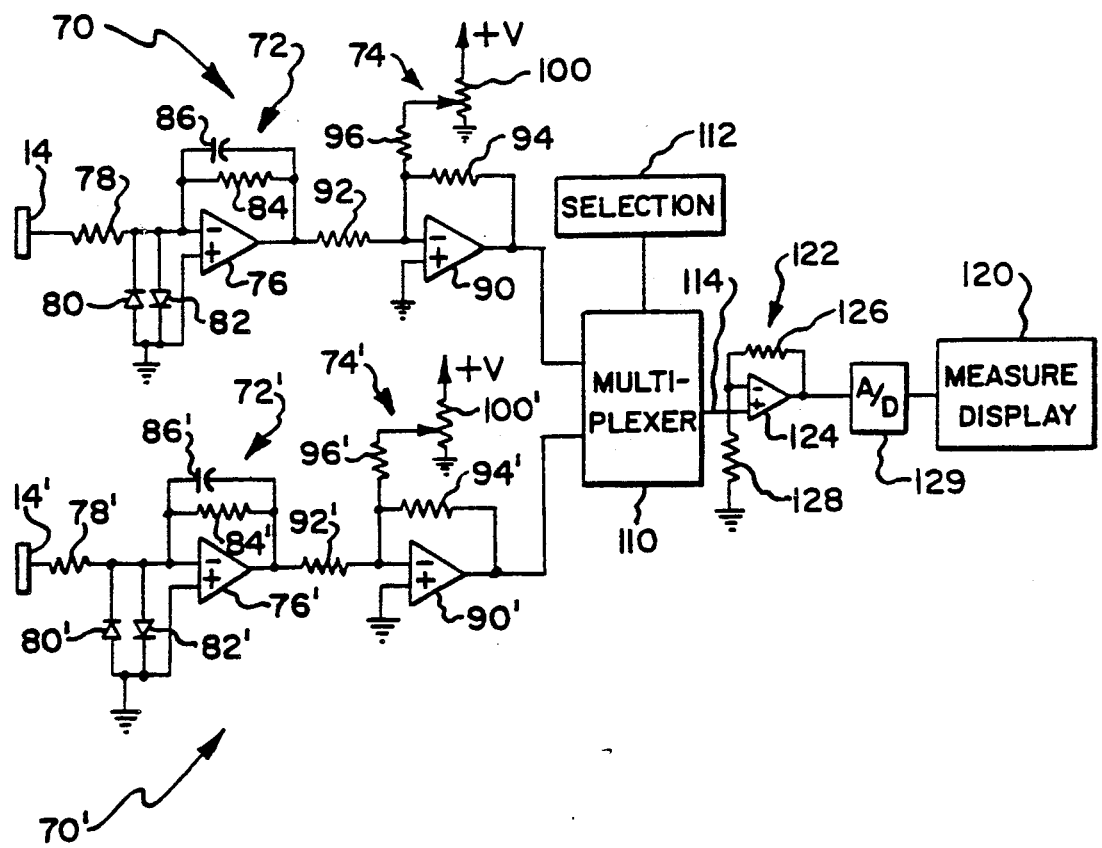
FIG. 4 is schematic circuit diagram of the circuit for detecting current signals induced in the sensing electrodes.

Referring now to FIG. 4, the apparatus of the present invention further comprises circuit means generally designated 70 connected to the sensing electrodes 14 for detecting current signals induced in the electrodes in response to variations in the surface charge crossing the edges of the electrodes. In particular, circuit means 70 includes a current to voltage conversion or averaging stage 72 and an amplication stage 74, and there is provided a circuit means 70 for each sensing electrode 14. As shown in FIG. 4, conversion stage 72 includes a differential amplifier 76, the inverting input of which is connected through an input resistor 78 to sensing electrode 14. The non-inverting input of amplifier 76 is connected to an electrical ground or reference, and a pair of parallel, oppositely-poled diodes 80, 82 are connected across the amplifier inputs. The output of amplifier 76 is connected through the parallel combination of resistor 84 and capacitor 86 to the amplifier inverting input terminal. Amplification stage 74 includes a differential amplifier 90, the inverting input of which is connected through a resistor 92 to the output of amplifier 76 of the conversion stage. The non-inverting input of amplifier 90 is connected to an electrical ground or reference. The output of amplifier 90 is connected to one end of a voltage divider comprising the series combination of resistors 24 and 96. The other end of the voltage divider is connected to the wiper arm of a potentiometer 100 serving as an adjustable voltage source and connected between a source of positive DC voltage and ground. An intermediate point on the voltage divider, in particular the junction of resistors 94 and 96, is connected by line 104 to the inverting input terminal of amplifier 90.

As show in FIG. 4, there is provided an identical circuit means for each sensing electrode, for example circuit means 70' for sensing electrode 14' and including identical component each designated by the same reference numerals provided with a prime superscript. Accordingly, for the illustrative arrangement previously described including 12 sensing electrodes, there would be provided 12 circuit means each identical to circuit means 70.

The apparatus of the present invention further includes scanning means generally designated 110 operatively connected to the circuit means for scanning the detected current signals. The scanning means 110 preferably comprises a multiplexer having an input connected to the output of circuit means 70, control or selection inputs connected to a source of control signals 112 and an output 114 in a typical arrangement including a large number of sensing electrodes, several multiplexers are provided, each one being associated with a group of sensing electrodes and corresponding circuit means in a manner which will be described.

The apparatus of the present invention also includes means generally designated 120 operatively connected to scanning means 110 for measuring at least one electrical parameter of the scanned signals to provide information on the charge density of surface 12 to determine the physical uniformity of surface 12. As shown in FIG. 4, the output of multiplexer 110 is connected through a buffer 122 to an input of measuring means 120. Buffer 122 comprises a differential amplifier 124, the non-inverting input of which is connected to the output of multiplexer 110. The output of amplifier 124 is connected through a resistor 126 to the inverting input which, in turn, is connected through a resistor 128 to an electrical ground. The output of buffer 122 is converted to the input of an analog-to-digital converter 129, the output of which is converted to measuring means which can comprise, for example, a video display or a computer. The former can provide a visual display of pulses having amplitudes indicative of variations in surface layer directly associated with surface defects in a manner which will be described. The latter can provide a histogram containing information as to size, location, and number of surface defects in a manner which will be described.

Figure 3:
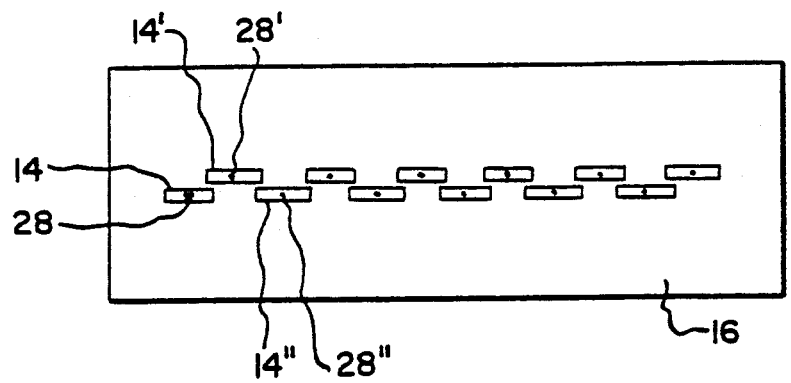
FIG. 3 is a schematic diagram illustrating the arrangement of sensing electrode in the apparatus of FIG. 1.

By way of example, in an illustrative apparatus including 48 sensing electrodes arranged in a manner like that of FIG. 3, there would be four scanning means 110 each associated with 12 sensing electrodes. Assuming consecutively numbered electrodes 14 extending along board 16, electrodes Nos. 1 through 4 would be associated with corresponding ones of the four scanning means 110, electrodes 5 through 8 would be associated corresponding ones of the scanning means 110, etc. By way of example, each scanning means is an AD8526A microprocessor. The circuit means 70 of electrodes Nos. 1 through 4 are connected to the S1 ports of the four microprocessors, the circuit means 70 of electrodes Nos. 5 through 8 are connected to the S2 ports thereof, etc. up to the S12 ports. The AO-A3 ports of the four microprocessors are connected together as are the WR, EN and RS ports. The D port of each microprocessor is connected to the corresponding buffer.

In the foregoing illustrative arrangement, buffer amplifiers 124 are type AD712, differential amplifiers 70 and 76 are type OPA484KU, resistors 94 and 96 both have magnitudes of 10K, potentiometer 100 has a maximum voltage of about 15 volts, resistor 78 has a magnitude of 1K and resistor 84 has a magnitude of 10 Megohms.

The illustrative apparatus of FIGS. 1 through 4 operates in the following manner. Drum 10 is rotated by drive motor 60 and charging means 40 is operated to apply electrical charge to drum surface 12 in a known manner. Typically, about 390 volts DC is applied to drum 10. Charge is applied to the entire portion of surface 12 which is to be inspected or measured. Board 16 is moved to place sensing electrode 14 in close proximity to drum surface 12 as shown in FIGS. 1 and 2. Drum 10 is rotated clockwise as viewed in FIG. 1 so that the edge 18 of each sensing electrode is first exposed to charge s surface 12 passes relative to electrode 14.

The basic principle of the measurement relies on the relationship $q = CV$ where "q" is the charge coupled into a sensitive electrode 14 (sensor) from the surface 12 to be measured. "C" is the capacitive coupling to the surface and "V" is the voltage difference between the surface 12 and the sensor 14. Moving the surface 12 past the sensor 14 at a fixed distance gives $$i = C \, dV/dt$$

where "i" is the current in the sensor 14. "C" is the capacitive coupling between the surface 12 and the sensor 14 and "dV/dt" is the rate of change of the voltage on the surface 12.

The spacing between the detector 14 and the drum surface 12 should be constant and on the order of 100 microns or less. A defect moving past the detector 14 will induce a current in the detector because the charge crossing the edge 18 of the detector per unit time will vary, due to $i = C \, dV/dt$ where V is the voltage on the drum surface 12 and C is the capacitive coupling of the sensor 14. The noise picked up by each detector 14 having dimensions $0.381 \, mm \times 6 \, mm$ is relatively small because the area is only $2.286 \, mm^2$. The signal is proportional to the speed at which the pin hole or defect crosses the edge 18 of the detector. In other words, since $i = c \, dV/dt = C(dV/dx)(dx/dt)$, the signal i is proportional to dx/dt, the speed at which the surface defect crosses edge 18 of sensing electrode 14. Maintaining the distance between the drum surface 12 and the detector 14 at a constant distance is important so that the signal i is proportional only to dV/dx and dx/dt.

As previously described, multiple sensors 14 are employed and digitally scanned in a drum sensor system. In a typical system there may be 12 to 128 sensors, more or less. The sensors 14 may be fabricated by known printed circuit techniques on one side of a circuit board 16 as previously described. The detection circuitry necessary for each sensor 14 can be placed on the other side of the printed circuit board 16. Each sensor 14 is the sensing element and input to the inverting mode of the circuit shown in FIG. 4. The geometry of each sensor electrode 14 is typically 0.4 mm by 6 mm as previously described. The long dimension is located perpendicular to the direction of motion of the drum 10 to provide sufficient room for the circuits on the opposite side of board 16.

The signal generated at the output of the circuit 70 shown in FIG. 4 is:

$$i = C_h dV/dt$$

where $C_h$ is the capacitance of the hole to the sensor. For 100 microns $\times$ 100 microns hole (defect) Ch can be approximated as a parallel plate capacitor:

$$C_h = C_o A/D = 8.85 \times 10^{-12} (10^{-4})^2/7.62 \times 10^{-5}$$

$$C_h = 10^{-15} \text{ farads}$$

If dV = 100 volts and an 8 cm diameter drum is rotatiOg at 2 revolutions per second, dt is $5 \times 10^{-5}$ seconds and $$i = (10^{-15} \text{ farads}) 100 \text{ Volts}/5 \times 10^{-5} \text{ sec} = 2 \times 10^{-9} \text{ amperes}$$

This magnitude Of current is easily measured. If the area of the hole is reduced by a factor of 16 corresponding to a 25u by 25u defect, the current generated would be approximately 125pA. These current levels can be measured easily at a rate of more than 100k sample/sec. The readings from a typical drum form a matrix of numbers typically 48 by 15,000. This array of numbers contains the information necessary to locate all the effective pin holes or defects on a surface 200 mm $\times$ 280 mm or an equivalent area corresponding to the drum 10 having an axial length of 28 cm and a diameter of 8 cm. The size of the effective pin hole (defect) in this case is 50u by 50u and a $\Delta V = 50$ Volts.

Figure 5:
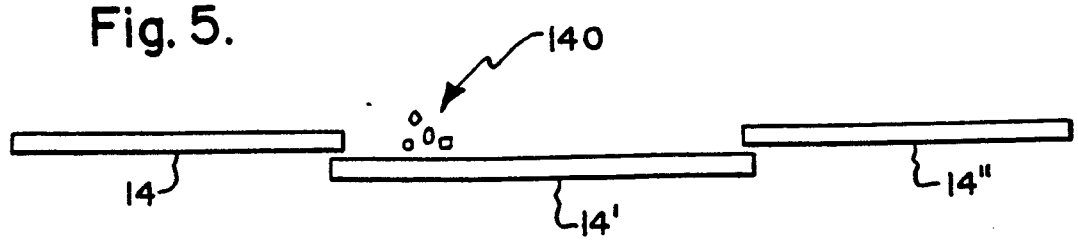
FIG. 5 is a schematic diagram illustrating the relationship between surface defects and the sensing electrodes.

FIG. 5 shows three sensing electrodes or detectors 14, 14', 14" which typically are offset from each other as previously described with a group or pattern 140 or surface holes or defects about to infringe on the edge 18" of sensing electrode 14'.

The current signals induced in sensing electrode 14 in response to surface holes or defects have several electrical parameters which can be inspected or measured to provide information as to the holes or defects. Pulse amplitude provides a measure of hole size, in particular the width of the hole. Pulse width also provides a measure of the hole size, in particular the length of the hole. For a more detailed description, reference may be made to pending U.S. Pat. Application of Peter R. Bossard and Jerzy Kieres filed this same data and entitled "Pin Hole Detector" HRAWG File No. 1,459.0008, the disclosure of which is hereby incorporated by reference.

Current pulses induced in the sensing electrodes 14 in response to movement of surface 12 relative thereto can be arranged in matrix as previously described by means of a computer to form a histogram. The horizontal axis contains points corresponding to the location of each the sensing electrodes along the one dimension of the surface being measured, i.e. the axial length of drum 10. The vertical axis contains points corresponding to the number of holes or defects sensed during travel of the electrode 14 along the other dimension of the surface, i.e. along the circumference of the drum 10.

Figure 6:
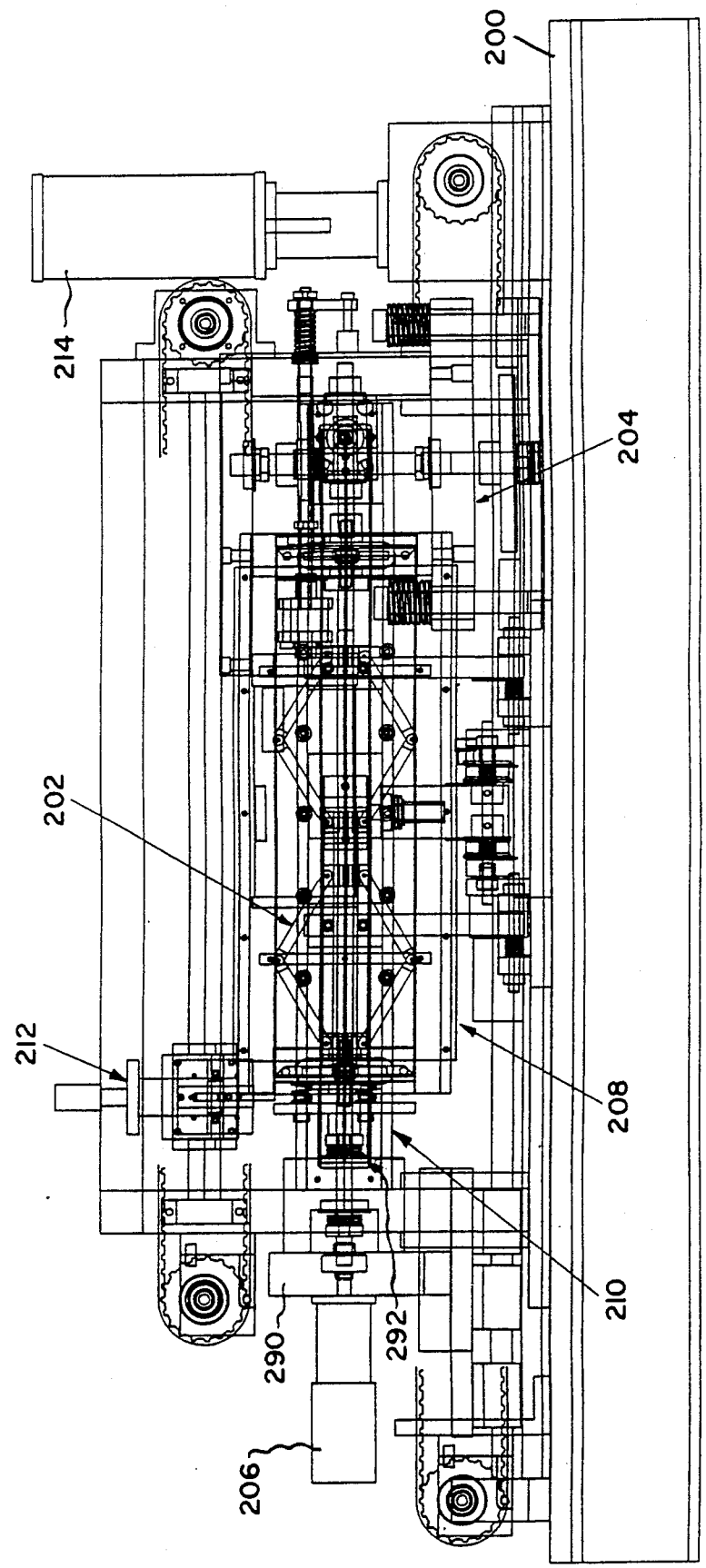
FIG. 6 is a front elevational of a preferred form of apparatus according to the present invention.
Figure 7:
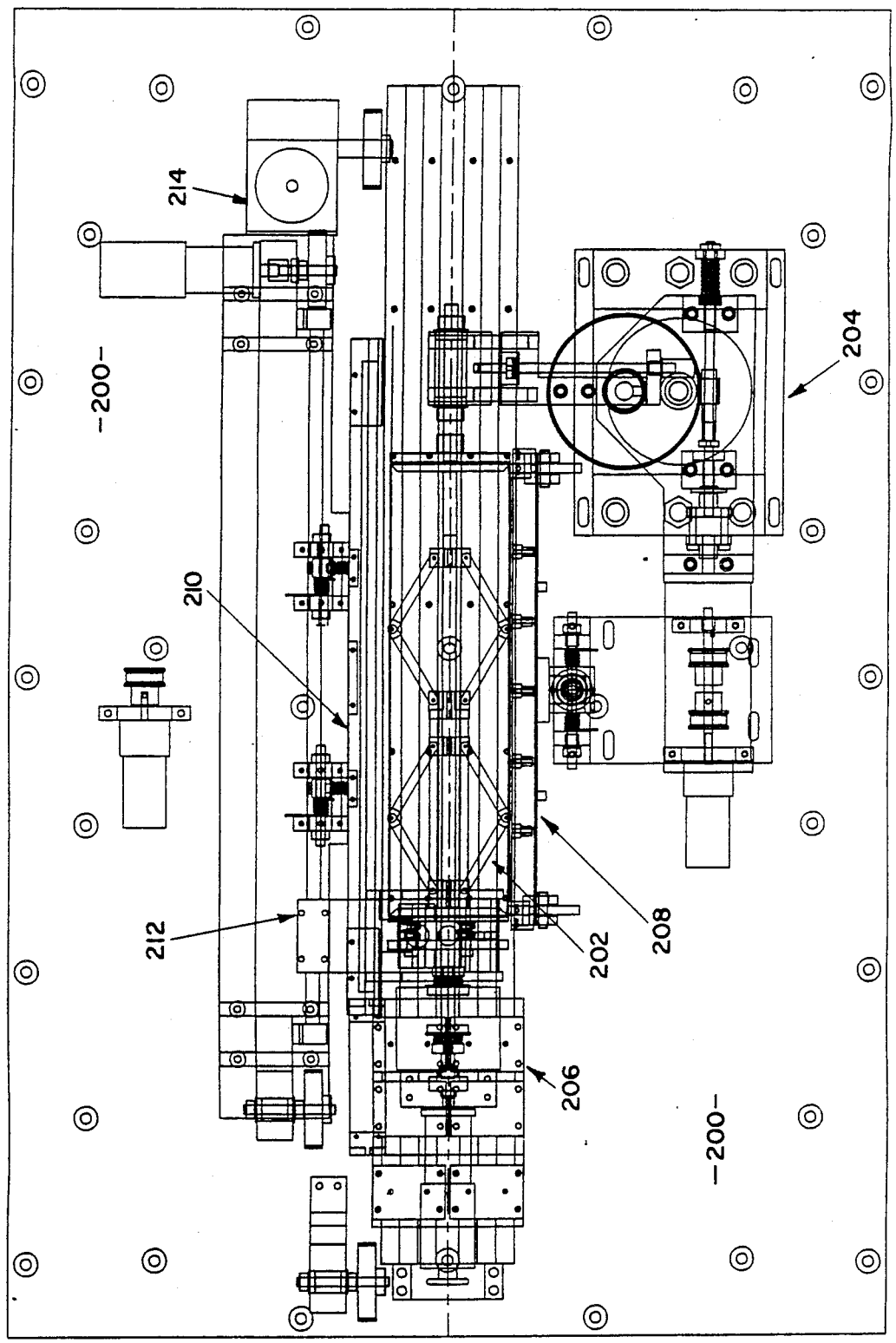
FIG. 7 is a tap plan view thereof.
Figure 8:
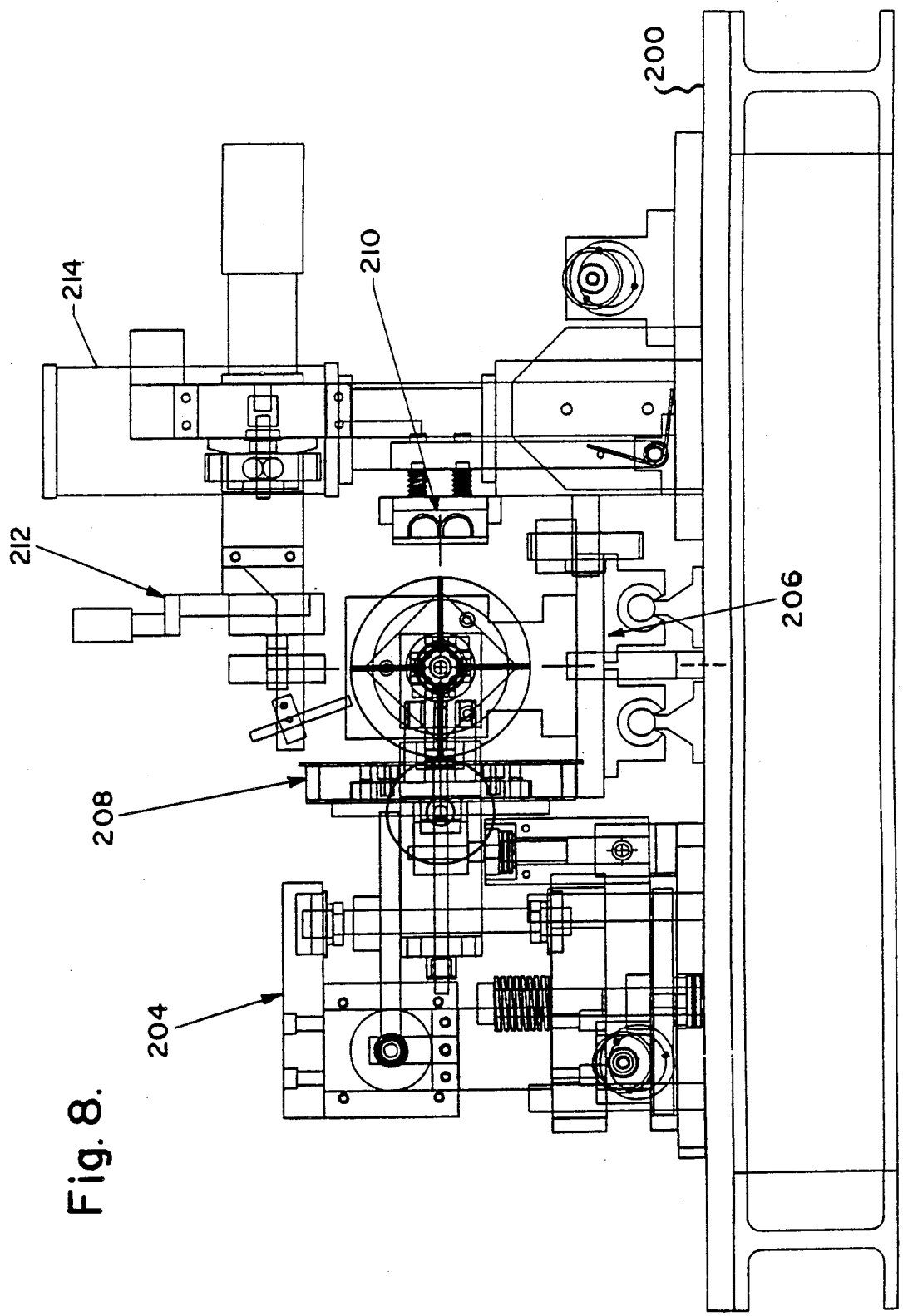
FIG. 8 is an end elevational view thereof.

FIGS. 6 through 20 illustrate a preferred form of the apparatus of the present invention wherein the entire apparatus is shown in the front, top and end views of FIGS. 6, 7, and 8, respectively, and wherein portions of the apparatus are shown in further detail in FIGS. 9 through 20. Referring first to FIGS. 6-20, the apparatus is supported on a base 200, and a drum to be inspected is received on a drum quide assembly 202 and held therein by a drum capture mechanism 204. The drum is rotated by a main drum drive motor 206, and a detector assembly 208 containing the sensing electrodes 14 and circuits previously described is moved into close physical proximity to the drum surface enabling defects to be sensed in the manner previously described. A drum charging assembly 210 is provided for applying electrical charge to the drum in connection with the inspection operation in a manner similar to charging apparatus 40 previously described. A probe slide assembly 212 movably carries the probe of an electrostatic voltmeter (not shown) For measuring the drum potential when desired. When the inspection operation on a drum is completed, it is removed from the apparatus by a mechanism including a drum eject drive 214. The apparatus then is ready to receive the next drum for inspecting the surface thereof.

Figure 11:
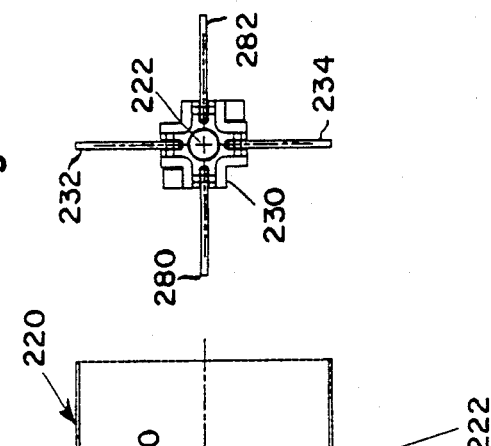
FIG. 11 is an elevation view of the opposite end thereof.
Figure 9:
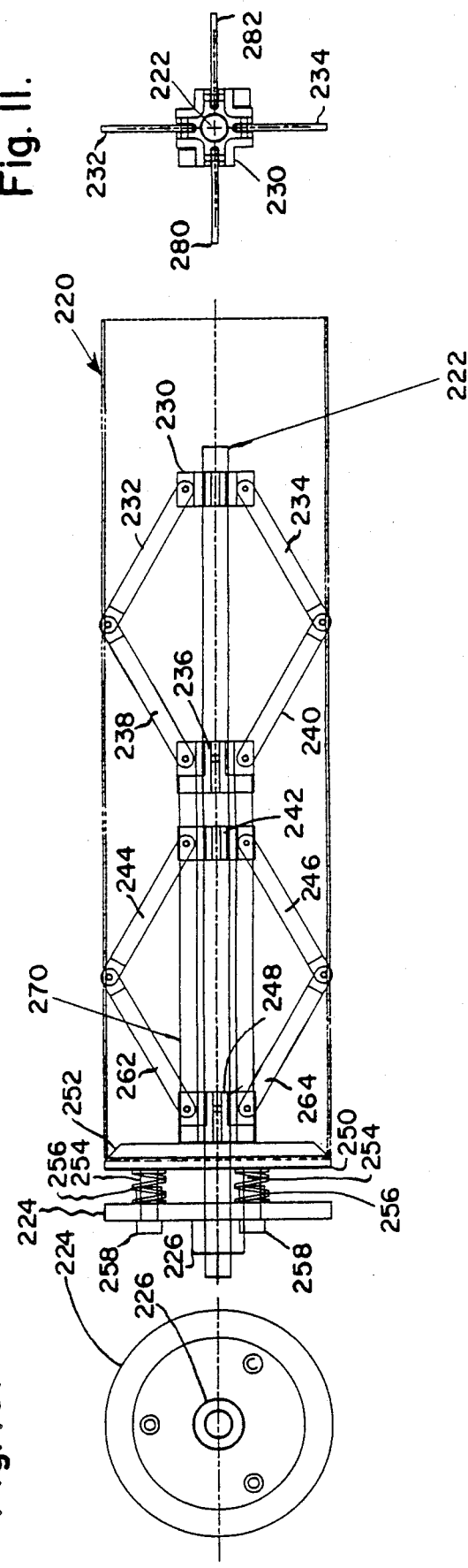
FIG. 9 is an enlarged side elevational view of the drum guide assembly and retention mechanism of the apparatus of FIGS. 6–18.
Figure 10:
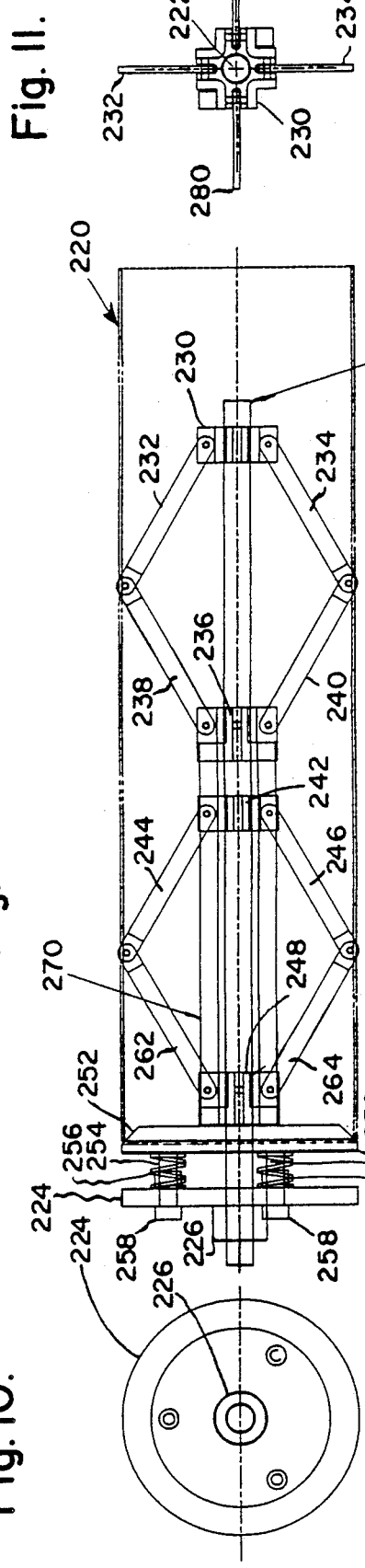
FIG. 10 is an elevational view of one end thereof.

FIGS. 9-11 illustrate in further detail the drum quide assembly and retention mechanism 202 for holding a drum, indicated at 220 in FIG. 6, in the apparatus for operation thereof. Drum 220 is held concentrically relative to a shaft 222 having one end within drum 220 and having the other end fixed to a disc-shaped member 224 having a central boss or extension 226 for coupling to drive motor 206 in a manner which will be described. Drum 220 is held on shaft 222 by a movable retention mechanism in the following manner. A first bracket 20 is fixed to the one end of shaft 222 and a first pair of retainer arms 232, 234 are pivotally connected at the end thereof to bracket 230 at diametrically opposite locations relative to shaft 222. A second bracket 236 is slidably located on shaft 222 axially inwardly of bracket 230. A second pair of retainer arms 238, 240 are pivotally connected at the ends thereof to bracket 236 at diametrically opposite locations relative to shaft 222. The other ends of retainer arms 232 and 238 are pivotally connected to each other. As a result, all four arms 232, 234, 238, and 240 lie in substantially the same place.

A third bracket 242 is fixed to shaft 222 at a location axially adjacent bracket 236. A third pair of retainer arms 244, 246 are pivotally connected at the ends thereof to bracket 242 at diametrically opposite locations relative the shaft 222. A fourth bracket 248 is provided on shaft 222 and is fixed to a circular end plate 250 which is concentrically and movably mounted on shaft 222. The one end of drum 220 abuts against a bevelled edge 252 formed around the periphery of plate 250. Plate 250 is coupled to member 224 by biasing means comprising bolts 254 extending through apertures in member 224 and fixed to plate 250 and biasing springs 246 Carried by bolts 254 and positioned between plate 250 and member 224, the extent of relative movement being limited by the bolt heads 258. A fourth pair of retainer arms 262, 248 are pivotally connected at the ends thereof to bracket 248 at diametrically opposite locations relative to shaft 222. The other ends of retainer arms 262 and 244 are pivotally connected to each other and, similarly the other ends of retainer arms 264 and 246 are pivotally connected to each other. As a result, all four arms 244, 246, 262 and 264 lie in substantially the same plane.

The three brackets 236, 242, and 248 are fixed to a square shaft structure generally designated 270 which is located radially outwardly of shaft 222 and comprises a plurality of bars, which are indicated at 272 and 274 in FIG. 9. The bars 272, 274 are fixed to plate 250 and to brackets 236, 242, and 248.

A similar arrangement of co-planar retainer arms is provided at ninety degrees to those shown in FIG. 9 and two of those additional retainer arms are designated 280 and 282 in FIG. 11.

As shown in FIG. 9, when drum 220 is placed on the retainer assembly, either manually or by robotic or other automatic means, the one end of drum 220 abuts plate 250 and the other, pivotally connected ends of the retainer arms contact or engage the inner surface of the drum. The drum capture mechanism 204, which will be described, moves a rotatable plate member similar to plate 250 into contact with the opposite end of drum 220. Continued movement of that member with force applied by the drum capture mechanism 204 causes drum 220 and plate 250 to move toward member 224 against the force of springs 256. As a result, the distance between plate 250 and member 224 decreases. Since bracket 242 is fixed to the square-shaft structure 270 and to shaft 222 and bracket 248 is fixed to plate 250, the distance between brackets 242 and 248 increases. Since bracket 236 is fixed to the square-shaft structure 270 and movable on shaft 222 and bracket 230 is fixed to the shaft 222, the distance between brackets 230 and 236 increases. As a result, the assembly of retainer arms is collapsed or moved slightly inwardly and out of contact with drum 220 thereby allowing the drum to be rotated in the following manner.

As previously described, the plate number of the drum capture mechanism 204 which contacts the one end of drum 220, i.e. The right-hand end as viewed by FIG. 9, is rotatably mounted on the drum capture mechanism and therefore rotates with drum 220. Rotational drive is transmitted from main drum drive motor 206 to plate 250 for rotating drum 220 in the following manner. As shown in FIG. 6, motor 206 is mounted on a bracket 290 which is fixed to the slide table of the drum eject mechanism which will be described. The output drive shaft of motor 206 is coupled by a shaft coupling assembly generally designated 292 to boss 226 of member 224 which, by virtue of screws 254, is rotationally fixed to plate 250. As a result, motor 206 operates to rotate member 224 and plate 250 together. Drum 220, being frictionally held between plate 250 and the corresponding plate of the drum capture mechanism 204, is thereby rotated by motor 206.

The drum capture mechanism 204 is shown in further detail in FIGS. 12, 13, and 14 which are front, top, and end views, respectively. The plate member thereof mentioned in the foregoing description is designated 300 and is substantially identical to plate 250 in the assembly of FIG. 6. In particular, plate 300 has a beveled edge 302 formed around the periphery thereof for contacting the end of drum 220. Plate 300 is movable between a position shown in FIG. 13 contacting the end of drum 220 and a portion removed from the end of drum 220, i.e. pivoted about 90° in a clockwise direction in FIG. 13, by the following arrangement. Plate 300 is fixed to one end of a shaft 304 which is journalled in a bearing assembly 306. The rotational axis of shaft 304 and center of the disc-shaped plate 300 are co-incident. Bearing 306 is adjustably movably carried by the end of an arm 310 of the drum capture mechanism. In particular, arm 310 is L-shaped wherein the foot 312 thereof extends generally parallel to the axis of shaft 304 and the leg 314 thereof extends substantially perpendicular to the axis of shaft 304. Bearing assembly 306 is movably connected to foot 312 by a series of bolts or heavy pins 316 which are firmly but movably received in recesses provided in the body of bearing assembly 306 and the surface of foot 312 facing bearing 306.

The centerline 320 or axis of rotation of shaft 304 is adjusted in the plane of the paper as viewed in FIG. 13, i.e. toward and away from arm 310, by first adjustment means including a shaft 322 which at one end is connected in the body of bearing assembly 306 in a manner permitting relative rotational movement but preventing relative axial movement. Shaft 322 extends through foot 312 and is threaded therein as indicated at 326. The opposite end of shaft 322 is rotatably supported in a bracket extension 328 of arm 310 and terminates in a fitting 320. Turning of shaft 322 by enqaqinq fitting 328 with an appropriate tool or by hand moves bearing assembly 306 toward or away from arm 310 depending upon the direction of rotation of shaft 322. This, in turn, adjusts the location of centerline 320 in the direction of arrow 332 in FIG. 13.

Arm 310 is pivoted to move plate 300 into and out of contact with the end of the drum in the following manner. Arm 310 is fixed to a shaft 336 which is journalled at one end, i.e. The upper end as viewed in FIGS. 12 and 14, in a bearing 338 mounted in an upper frame member 340. Shaft 336 is journalled at the opposite or lower and in a bearing 342 mounted in a lower frame member 344. The upper and lower Frame members 340 and 344, respectively, are joined by vertically disposed, spaced apart side frame members 346, 348 as viewed in FIG. 12. A worm gear 350 is fixed to shaft 336 and is in meshing engagement with a worm 352 fixed to a shaft 356 journalled in bearings in side frames 346, 348 and coupled by a slip coupling 360 to the output shaft of a drive motor 362. Motor 362 is supported by a bracket 364 fixed to upper frame member 340. A biasing force is applied to shaft 356 by a spring 368 supported by a bracket 370 fixed to frame member 348, the biasing force ensuring proper meshing engagement between worm 352 and gear 350.

Thus, depending upon the commanded direction of output drive from motor 362, worm 352 is driven to rotate gear 350 in either direction and with it shaft 336 to pivot arm 310 about the axis of shaft 336. Clockwise rotation of gear 350 pivots arm 310 to swing plate 300 along an arc in a clockwise direction as viewed in FIG. 13 and move plate 300 away from the end of drum 220. Counterclockwise rotation of gear 350 pivots arm 310 to swing plate along a counterclockwise arc as viewed in FIG. 13 to move plate 300 into contact with the end of drum 220. Once contact is made, continued operation of motor 362 in the same direction causes further movement of plate 300 against drum 220 forcing it toward member 224 to collapse the retainer arms as previously described.

The centerline 320 or axis of rotation of shaft 304 is adjusted in the plane of the paper as viewed in FIG. 12, i.e. toward and away from base 200, by second adjustment means including a platform 380 below the lower frame member 344 and connected thereto by screws 382 threaded in frame member 344 and rotatably mounted in platform 380. Screws 382 are mounted in platform 380 in a manner preventing relative axial movement. Platform 380 is fixed to base 200. Biasing springs 384 engage the heads of screws 382 and the surface of frame 344. Turning screws 382 move frame 344 toward or away from platform 380 thereby adjusting centerline 320 in the direction of arrow 388 in FIG. 12. The adjustments of the axis of rotation of shaft 304 in the two directions of arrows 332 and 388 ensures proper alignment of that axis with the axis of the drum 220 to provide uniform rotation of drum 220 during the inspection operation.

The detector assembly 208 is shown in further detail in FIGS. 15-17 wherein FIG. 15 shows the side of the assembly which faces drum 220 and FIGS. 16 and 17 are top and end views, respectively. The detector assembly includes sensing means generally designated 400 having a surface adopted to face the drum 220. The sensing means typically is in the form of circuit board 16 and the plurality of sensing electrodes 14 arranged thereon as previously described. In the assembly shown, the circuit board of sensing means 400 is attached to an elongated rectangular supporting frame 402 by fasteners 404. During operation of the apparatus to inspect the surface of drum 220, sensing means 400 is placed in close physical proximity to the drum surface as previously described. There is provided means for maintaining a predetermined constant spacing between sensing means 400 and the surface of drum 220 being inspected. A pair of guide wheel assemblies 408 and 410 are carried by frame 402 at opposite ends thereof. The rotatable quide wheels 412 and 414 are located to contact the outer surface of drum 220 as shown in FIG. 17 when sensing means 400 is closely spaced to the drum 220. In being rotatably mounted on frame 402, quide wheels 412, 414 maintain a constant spacing between sensing means 400 and the outer surface of drum 220 as it rotates. The quide wheel assemblies 408, 410 are adjustably mounted on frame 402 by screws or the like to enable adjustment of the spacing between sensing means 400 and the drum surface. Adjustment screws 418 are provided in frame 402 and engage the circuit board of sensing means 400 for the purpose of keeping the board and hence the sensing electrodes thereon in a flat condition for proper sensing operation.

Sensing means 400 is mounted for movement toward and away from the drum surface in a first degree of freedom by the following arrangement. A platform 424 is fixed to base 200 and is provided with a pair of upstanding brackets 426, 428 in which a shaft 430 is rotatably mounted. A post 432 is fixedly mounted at one end, i.e. The lower end as viewed in FIGS. 15 and 17, to shaft 430 intermediate the ends thereof and between brackets 426, 428. The other end of post 432, i.e. The upper end as viewed in FIGS. 15 and 17 is connected to frame 402 by means of a pivot bearing 434 connected to post 432 and to a bracket 436 fixed to frame 402. As a result, sensing means 400 is movable toward and away from the surface of drum 220, in particular being mounted for pivotal movement about the axis of shaft 430 which is parallel to the lonqitudinal axis of rotation of drum 220. This pivotal movement is indicated by arrows 438 in FIG. 17.

Sensing means 400 is mounted for movement in a second degree of freedom, i.e. for pivotal movement about an axis substantially perpendicular to the axis of rotation of drum 220, by the provision of pivot bearing 434. Bearing 434 has a body removably mounted in post 432. A shaft 440 journalled in the body of bearing 434 is connected to bracket 436. Accordingly, frame 402 is pivotally movable about the axis of bearing shaft 440 in the direction of arrows 442 in FIG. 16. This degree of freedom allows sensing means 400 to accommodate any irregularities in drum geometry as it rotates during inspection thereof.

There is provided means for moving sensing means 400 toward the surface of drum 220 for inspection thereof and for moving sensing means 400 away from the surface of drum 220 upon completion of inspection to allow ejection of drum 220. A pair of coil springs 450, 452 are provided on shaft 430. One end of each spring is fixed to a corresponding one of the brackets 426, 428. The other end of each spring is fixed to post 432. As a result, springs 450, 452 apply a biasing force to post 432 and thus to frame 402 to urge sensing means 402 toward the surface of drum 220.

For moving sensing means 400 away from drum 220 there is provided an arrangement including a shaft 458 journalled in bearing blocks 460, 432 mounted on platform 424. Shaft 458 is disposed parallel to shaft 430. One end of shaft 458 is connected to the output drive shaft of a motor 46A mounted on platform 424. A pair of spools 468, 470 are mounted in spaced relation on shaft 458 inwardly of bearing blocks 460, 462. A first line 47A is wound on spool 468 and fastened to frame 402, and a second line 476 is wound on spool 470 and fastened to frame 402. Lines 474, 476 are of flexible cord or fine wire. When it is desired to move sensing means 400 away from drum 220, motor 464 is operated to rotate spools 468, 470 in a direction tightening lines 474, 476 to pivot frame 402 about shaft 430 in a direction away from sensing means and against the force of springs 450, 452.

The drum eject mechanism is shown in detail in FIGS. 18-20 and operates to move drum 220 while held by the drum retention mechanism to a location for removal from the apparatus after an inspection operation. The drum eject mechanism includes a linear slide 484 mounted on base 200. Slide 484 defines a plurality of tracks along the drum ejector path, and a slide table 490 is movably supported on slide 484 for movement thereby guided by the tracks. The arrangement of drum 220, the drum retention mechanism, drum drive motor Z06, coupling assembly 292, and bracket 290 is carried by slide table 490, bracket 290 being mounted thereon. Slide table 490 is moved from the location shown in FIG. 18, where drum 220 is located during the inspection operation, to a drum removal or ejector location to the right as viewed in FIG. 18. This is accomplished by a belt drive arrangement operated by drum eject drive motor 214 in the following manner. Gear 496 is located near one end of slide 484. A second gear 304 is journalled in a bracket 503 located near the opposite end of slide 484. A toothed belt 510 trained around gears 496 and 504 and one point along belt 510 to move slide table 490 to the right as viewed in FIG. 18 to eject an inspected drum. While at that location, the drum retention mechanism can receive the next drum to be inspected. Then, operation of motor 214 in the opposite direction rotates belt 510 in the opposite direction to return the slide table 490 to the location of FIG. 18 for beginning of the next inspection operation.

Motors 206, 214, 362, and 464 are connected to an appropriate control for controlling the operation thereof to perform the various operations previously described. An appropriate senser associated with the drum drive motor is connected to the control to provide information on the number of drum rotations so that completion of the inspection is signalled. An appropriate arrangement of position sensors associated with arm 310 is connected to the control for monitoring operation of the clamping assembly. Similar arrangements of position sensors are associated with frame 402 and with slide table 490.

It is therefore apparent that the present invention accomplishes its intended objects. While an embodiment of the present invention has been described in detail, that is for the purpose of illustration, not limitation.

We claim:

1. Apparatus for electrically inspecting the surface of a drum capable of holding electrical charge comprising:
   a) means for applying electrical charge to the surface of said drum;
   b) a detector assembly including electrical sensing means responsive to variation in the charge on said drum surface, said electrical sensing means comprising electrode means having an edge and disposed so that upon relative movement between said drum surface and said electrode means charge on said drum surface crosses said edge of said electrode means;
   c) means for moving said detector assembly to place said sensing means in close proximity to said drum surface;
   d) means for mounting said detector assembly for pivotal movement about an axis substantially perpendicular to the axis of rotation of said drum to accommodate variations in drum geometry; and
   e) means for rotating said drum during inspection thereof so that current signals are induced in said sensing electrode means in response to a variation in the surface charge crossing said edge for providing information relating to said surface.

2. Apparatus according to claim 1, further including means for moving said sensing means away from said drum after inspection thereof.

3. Apparatus according to claim 1, wherein said detector assembly is mounted for pivotal movement about an axis substantially parallel to the axis of rotation of said drum during movement of said detector assembly into proximity with said drum surface.

4. Apparatus for electrically inspecting the surface of a drum capable of holding electrical charge comprising:
   a) means for applying electrical charge to the surface of said drum;
   b) a detector assembly including electrical sensing means responsive to variation in the charge on said drum surface, said electrical sensing means comprising electrode means having an edge and disposed so that upon relative movement between said drum surface and said electrode means charge on said drum surface crosses said edge of said electrode means;
   c) means for moving said detector assembly to place said sensing means in close proximity to said drum surface;
   d) means on said detector assembly and operatively contacting said drum for maintaining constant spacing between said sensing means and said drum surface during rotation of said drum; and
   e) means for rotating said drum during inspection thereof so that current signals are induced in said sensing electrode means in response to a variation in the surface charge crossing said edge for providing information relative to said surface.

5. Apparatus according to claim 4, further including means for moving said sensing means away from said drum after inspection thereof.

6. Apparatus for electrically inspecting the surface of a drum capable of holding electrical charge comprising:
   a) means for applying electrical charge to the surface of said drum;
   b) a detector assembly including electrical sensing means responsive to variation in the charge on said drum surface, said electrical sensing means comprising electrode means having an edge and disposed so that upon relative movement between said drum surface and said electrode means charge on said drum surface crosses said edge of said electrode means;
   c) drum guiding and retention means for operatively contacting the inner surface of a drum to receive and hold a drum for inspection;
   d) drum clamping means for operatively engaging the ends of said drum during inspection thereof; and
   e) means for rotating said drum while engaged by said clamping means, so that current signals are induced in said sensing electrode means in response to a variation in the surface charge crossing said edge for providing information relating to said surface.

7. Apparatus according to claim 6, wherein said drum quiding and retention means includes a retainer arm assembly initially contacting the inner surface of said drum and movable out of contact with said drum inner surface in response to said clamping means engaging said drum.

8. Apparatus according to claim 6, wherein said drum clamping means includes adjustment means for moving a component of said clamping means to accommodate variation in drum geometry.

9. Apparatus according to claim 6 further including:
   a) means for moving said clamping means out of engagement with said drum after inspection thereof; and
   b) ejecting means operatively associated with said drum guiding and retention means for moving said guiding and retention means along with said drum away from said apparatus after inspection of said drum.

* * * * *